United States Patent
Burbank et al.

(10) Patent No.: US 7,329,265 B2
(45) Date of Patent: Feb. 12, 2008

(54) UTERINE ARTERY OCCLUSION CLAMP

(75) Inventors: Fred H. Burbank, Laguna Niguel, CA (US); Michael L. Jones, San Clemente, CA (US); Greig E. Altieri, Laguna Beach, CA (US)

(73) Assignee: Vascular Control Systems, Inc., San Juan Capistrano, CA (US)

( * ) Notice: Subject to any disclaimer, the term of this patent is extended or adjusted under 35 U.S.C. 154(b) by 397 days.

(21) Appl. No.: 10/430,880

(22) Filed: May 6, 2003

(65) Prior Publication Data
US 2004/0153105 A1 Aug. 5, 2004

Related U.S. Application Data

(63) Continuation-in-part of application No. 10/355,809, filed on Jan. 30, 2003.

(51) Int. Cl.
*A61B 17/08* (2006.01)
(52) U.S. Cl. .................................................. 606/157
(58) Field of Classification Search ................ 600/454, 600/455, 545; 606/119, 120, 151, 157, 158, 606/205
See application file for complete search history.

(56) References Cited

U.S. PATENT DOCUMENTS

| | | | |
|---|---|---|---|
| 2,400,251 A | 5/1946 | Nagel | |
| 3,209,753 A | 10/1965 | Hawkins et al. | |
| 3,411,505 A | 11/1968 | Nobis | |
| 3,777,740 A * | 12/1973 | Hokanson | 600/455 |
| 3,779,248 A | 12/1973 | Karman | |
| 4,120,302 A | 10/1978 | Ziegler | |
| 4,226,240 A | 10/1980 | Walker, Jr. | |
| 4,292,960 A | 10/1981 | Paglione | |
| 4,428,374 A | 1/1984 | Auburn | |
| 4,428,379 A | 1/1984 | Robbins et al. | |
| 4,509,528 A * | 4/1985 | Sahota | 600/504 |
| 4,650,466 A | 3/1987 | Luther | |
| 4,757,823 A | 7/1988 | Hofmeister et al. | |
| 4,945,896 A | 8/1990 | Gade | |

(Continued)

FOREIGN PATENT DOCUMENTS

DE 195 28 440 A 2/1997

(Continued)

OTHER PUBLICATIONS

International Search Report for PCT/US04/01935 mailed Feb. 15, 2005.

(Continued)

*Primary Examiner*—Anhtuan T. Nguyen
*Assistant Examiner*—Tuan V. Nguyen (57) ABSTRACT

The invention is directed to a uterine artery clamp and the relatively non-invasive treatment procedure utilizing this clamp. The uterine clamp includes a clamping member having a jaw with tissue-contacting surfaces for applying pressure to target tissue and a stabilizing member which is configured to be inserted into the patient's uterine cervical canal. The clamp may be provided with elongated handles to manually adjust the spacing between the jaw and stabilizer and thereby apply pressure to a uterine artery beneath a bundle of tissue held between the jaw and stabilizer. Uterine clamps embodying features of the invention by be used in procedures for treating uterine disorders such as fibroids, DUB, PPH and the like.

26 Claims, 3 Drawing Sheets

U.S. PATENT DOCUMENTS

| | | | |
|---|---|---|---|
| 4,991,588 A | 2/1991 | Pflueger et al. | |
| 4,994,069 A | 2/1991 | Ritchart et al. | |
| 5,037,433 A | 8/1991 | Wilk et al. | |
| 5,081,997 A | 1/1992 | Bosley, Jr. et al. | |
| 5,108,408 A | 4/1992 | Lally | |
| 5,201,314 A | 4/1993 | Bosley et al. | |
| 5,226,911 A | 7/1993 | Chee et al. | |
| 5,261,409 A | 11/1993 | Dardel | |
| 5,275,166 A * | 1/1994 | Vaitekunas et al. | 600/439 |
| 5,289,831 A | 3/1994 | Bosley | |
| 5,336,229 A | 8/1994 | Noda | |
| 5,336,231 A | 8/1994 | Adair | |
| 5,383,922 A | 1/1995 | Zipes et al. | |
| 5,427,108 A | 6/1995 | Bollinger | |
| 5,456,693 A | 10/1995 | Conston et al. | |
| 5,458,596 A | 10/1995 | Lax et al. | |
| 5,488,958 A | 2/1996 | Topel et al. | |
| 5,496,331 A | 3/1996 | Xu et al. | |
| 5,507,744 A | 4/1996 | Tay et al. | |
| 5,542,944 A | 8/1996 | Bhatta | |
| 5,549,624 A | 8/1996 | Mirigian et al. | |
| 5,549,824 A | 8/1996 | Trumpf et al. | |
| 5,556,396 A | 9/1996 | Cohen et al. | |
| 5,562,680 A * | 10/1996 | Hasson | 606/119 |
| 5,570,692 A | 11/1996 | Morinaga | |
| 5,582,617 A * | 12/1996 | Klieman et al. | 606/170 |
| 5,588,960 A | 12/1996 | Edwards et al. | |
| 5,591,173 A | 1/1997 | Schifano | |
| 5,598,841 A | 2/1997 | Taniji et al. | |
| 5,614,204 A | 3/1997 | Cochrum | |
| 5,658,299 A | 8/1997 | Hart | |
| 5,662,676 A | 9/1997 | Koninckx | |
| 5,662,680 A | 9/1997 | Desai | |
| 5,665,096 A | 9/1997 | Yoon | |
| 5,672,153 A | 9/1997 | Lax et al. | |
| 5,672,172 A | 9/1997 | Zupkas | |
| 5,674,243 A | 10/1997 | Hale | |
| 5,691,314 A | 11/1997 | Hodgen | |
| 5,697,937 A * | 12/1997 | Toma | 606/119 |
| 5,697,942 A | 12/1997 | Palti | |
| 5,702,407 A | 12/1997 | Kaji | |
| 5,713,371 A | 2/1998 | Sherman et al. | |
| 5,713,896 A | 2/1998 | Nardella | |
| 5,713,942 A | 2/1998 | Stern et al. | |
| 5,715,832 A | 2/1998 | Koblish et al. | |
| 5,716,389 A | 2/1998 | Walinsky et al. | |
| 5,720,743 A | 2/1998 | Bischof et al. | |
| 5,749,879 A | 5/1998 | Middleman et al. | |
| 5,759,154 A | 6/1998 | Hoyns | |
| 5,766,135 A | 6/1998 | Terwilliger | |
| 5,776,129 A | 7/1998 | Mersch | |
| 5,792,059 A | 8/1998 | Furia et al. | |
| 5,797,397 A | 8/1998 | Rosenberg | |
| 5,800,378 A | 9/1998 | Edwards et al. | |
| 5,817,022 A | 10/1998 | Vesely | |
| 5,836,906 A | 11/1998 | Edwards | |
| 5,840,033 A | 11/1998 | Takeuchi | |
| 5,895,386 A | 4/1999 | Odell et al. | |
| 5,895,395 A | 4/1999 | Yeung | |
| 5,899,861 A | 5/1999 | Friemel et al. | |
| 5,904,651 A | 5/1999 | Swanson et al. | |
| 5,910,484 A | 6/1999 | Haupert, Jr. | |
| 5,911,691 A | 6/1999 | Mochizuki et al. | |
| 5,916,173 A | 6/1999 | Kirsner | |
| 5,921,933 A | 7/1999 | Sarkis et al. | |
| 5,922,008 A | 7/1999 | Gimpelson | |
| 5,941,889 A | 8/1999 | Cermak | |
| 5,979,453 A | 11/1999 | Savage et al. | |
| 6,013,088 A | 1/2000 | Karavidas | |
| 6,015,541 A | 1/2000 | Greff et al. | |
| 6,019,724 A | 2/2000 | Gronningsaeter et al. | |
| 6,032,673 A | 3/2000 | Savage et al. | |
| 6,033,398 A | 3/2000 | Farley et al. | |
| 6,034,477 A | 3/2000 | Peeters et al. | |
| 6,035,238 A | 3/2000 | Ingle et al. | |
| 6,039,693 A | 3/2000 | Seward et al. | |
| 6,045,508 A | 4/2000 | Hossack et al. | |
| 6,066,139 A | 5/2000 | Ryan et al. | |
| 6,077,257 A | 6/2000 | Edwards et al. | |
| 6,080,118 A | 6/2000 | Blythe | |
| 6,096,051 A | 8/2000 | Kortenbach et al. | |
| 6,106,473 A | 8/2000 | Violante et al. | |
| 6,152,874 A | 11/2000 | Looney et al. | |
| 6,169,914 B1 | 1/2001 | Hovland et al. | |
| 6,175,751 B1 | 1/2001 | Maizes | |
| 6,186,947 B1 | 2/2001 | Ouchi | |
| 6,210,330 B1 | 4/2001 | Tepper | |
| 6,231,515 B1 | 5/2001 | Moore et al. | |
| 6,254,601 B1 | 7/2001 | Burbank et al. | |
| 6,261,234 B1 | 7/2001 | Lin | |
| 6,280,441 B1 | 8/2001 | Ryan | |
| 6,293,954 B1 * | 9/2001 | Fogarty et al. | 606/151 |
| 6,299,621 B1 | 10/2001 | Fogarty et al. | |
| 6,368,340 B2 * | 4/2002 | Malecki et al. | 606/204 |
| 6,371,973 B1 * | 4/2002 | Tepper | 606/205 |
| 6,425,867 B1 | 7/2002 | Vaezy et al. | |
| 6,602,251 B2 | 8/2003 | Burbank et al. | |
| 6,610,074 B2 | 8/2003 | Santilli | |
| 6,905,506 B2 * | 6/2005 | Burbank et al. | 606/205 |
| 2002/0111537 A1 | 8/2002 | Taylor et al. | |
| 2002/0165579 A1 | 11/2002 | Burbank et al. | |
| 2002/0183771 A1 | 12/2002 | Burbank et al. | |
| 2002/0188306 A1 | 12/2002 | Burbank et al. | |
| 2003/0018270 A1 | 1/2003 | Makin et al. | |
| 2003/0120306 A1 | 6/2003 | Burbank et al. | |

FOREIGN PATENT DOCUMENTS

| | | |
|---|---|---|
| DE | 200 22 012 U1 | 5/2001 |
| EP | 0 472 368 | 2/1992 |
| EP | 0 598 579 | 5/1994 |
| EP | 0 890 342 A | 1/1999 |
| EP | 1 072 282 | 1/2001 |
| FR | 1 220 773 A | 5/1960 |
| GB | 2 302 025 A | 1/1997 |
| GB | 2 311 468 A | 1/1997 |
| GB | 2302025 A * | 1/1997 |
| WO | WO 95/02370 | 1/1995 |
| WO | WO 95/02371 | 1/1995 |
| WO | WO 96/10365 | 4/1996 |
| WO | WO 97/27897 | 8/1997 |
| WO | WO 97/47246 | 12/1997 |
| WO | WO 98/19713 | 5/1998 |
| WO | WO 99/00057 | 1/1999 |
| WO | WO 99/11179 A | 3/1999 |
| WO | WO 01/68720 | 9/2001 |
| WO | WO 01/80713 | 11/2001 |
| WO | WO 02/00192 | 1/2002 |
| WO | WO 02/39904 A1 | 5/2002 |
| WO | WO 02/078521 | 10/2002 |

OTHER PUBLICATIONS

International Search Report for PCT/US2004/038276, mailed Mar. 15, 2005.
International Search Report for PCT/US2004/038111, mailed May 3, 2005.
Written Opinion for PCT/US2004/038111, mailed May 3, 2005.
Translation of FR 1 220 773.
International Preliminary Report of Patentability for Serial No. PCT/US04/01935, mailed Jul. 9, 2005.
Barth, Klemens H. et al., "Long Term Follow-Up of Transcatheter Embolization With Autologous Clot, Oxycel and Gelfoam in Domestic Swine", *Investigative Radiology*, May-Jun. 1977, vol. 12, pp. 273-290.

Bateman, William M.D., "Treatment of intractable menorrhagia by bilateral uterine vessel, Interruption", *Am. J. Obst. & Gynec.* 89(6):825-827 (Jul. 15, 1964).

Brigato, G. et al., "A Noninvasive Instrumental Method in Severe Postpartum Hemorrhages", *Minerva Ginecologica* 50(7-8):337-339 (1998).

Brohim, Robert M. et al., "Development of Independent Vessel Security After Ligation With Absorbable Sutures or Clips", *The American Journal of Surgery*, Mar. 1993, vol. 165, pp. 345-348.

Burbank, Fred et al., "Uterine Artery Occlusion by Embolization or Surgery for the Treatment of Fibroids: A Unifying Hypothesis-Transient Uterine Ischemia", *The Journal of the American Association of Gynecologic Laparoscopists*, Nov. 2000, vol. 7, No. 7 Supplemental, pp. S3-S49.

Fuchs, Karl, "Afibrinogenemia Treated by Ligation of Uterine Arteries", *Gynacologic* 148:407-411 (1959).

Garza Leal, J. et al., "Myoma Treatment by Transient Uterine Ischemia", *The Journal of the American Association of Gynecologic Laparoscopists* 7(3):S31 (Aug. 2000).

Hay, D.L. et al., "Hemostasis in Blood Vessels After Ligation", *Am. J. Obstet. Gynecol.*, Mar. 1989, 160:3, pp. 737-739.

Hunerbein, M. et al., "Endoscopic Ultrasound-Guided Real Time Biopsy of Peri-Intestinal Tumors", *Surgical Technology International VII*, 1998, pp. 91-95.

O'Leary, James A., M.D., "Uterine Artery Ligation in the Control of Postcesarean Hemorrhage", *The Journal of Reproductive Medicine, Inc.*, 40(3):189-193 (Mar. 1995).

O'Leary, James L., M.D. et al., "Uterine artery ligation in the control of intractable postpartum hemorrhage", Am. J. Obst. & Gynec. 94(7):920-924 (Apr. 1, 1966).

Ravina, J.H. et al., "Arterial Embolisation to Treat Uterine Myomata", *The Lancet*, Sep. 9, 1995, vol. 346, No. 8976, pp. 671-672.

Schaefer, C.J. et al., "Absorbable Ligating Clips", *Surg. Gynecol. Obstet.*, 1982, 154:513-516.

"Mick 200-TP Applicator Package", Mick Radio-Nuclear Instruments, Inc., advertisement.

"Multiplanar Biopsy Transverse Scan", Bruel & Kjaer Medical Systems, Inc., advertisement.

"Seeding Device—Proscan Urologic Ultrasound Imaging System", Teknar, advertisement.

Sonopsy Ultrasound Guided Breast Biopsy, NeoVision, advertisement.

"Transrectal Biopsy of the Prostrate Gland", Bruel & Kjaer Medical Systems, Inc., advertisement.

\* cited by examiner

UTERINE ARTERY OCCLUSION CLAMP

CROSS-REFERENCE TO RELATED APPLICATIONS

This application is a continuation-in-part of U.S. patent application Ser. No. 10/355,809, entitled "Devices and Methods for Treating Vaginal Delivery PPH", filed Jan. 30, 2003 which is hereby incorporated by reference in its entirety and from which priority is hereby claimed under 35 U.S.C. § 120.

FIELD OF THE INVENTION

The invention is generally directed to the treatment of uterine disorders by detecting and regulating blood flow through one or both of the patient's uterine arteries.

BACKGROUND OF THE INVENTION

Hysterectomy (surgical removal of the uterus) is performed on approximately 600,000 women annually in the United States. Hysterectomy is often the therapeutic choice for the treatment of uterine cancer, adenomyosis, menorrhagia, prolapse, dysfunctional uterine bleeding (abnormal menstrual bleeding that has no discrete anatomic explanation such as a tumor or growth), and muscular tumors of the uterus, known as leimyoma or uterine fibroids.

However, hysterectomy is a drastic treatment, having many undesirable characteristics. Thus, any method which can approximate the therapeutic result of a hysterectomy without removing the uterus would be a significant improvement in this field. Newer treatment methods have been developed for some diseases which may spare these women a hysterectomy.

In 1995, it was demonstrated that uterine fibroids could be treated without hysterectomy using a non-surgical therapy, specifically comprising bilateral intraluminal occlusion of the uterine arteries (Ravina et al., "Arterial Embolization to Treat Uterine Myomata", Lancet Sep. 9, 1995; Vol. 346; pp. 671-672, incorporated in its entirety herein). This technique is known as "uterine artery embolization". In this technique, uterine arteries are accessed via a transvascular route from a common femoral artery into the left and right uterine arteries by means of an intravascular catheter and embolic material, such as small metallic coils, polyvinyl alchohol particulate and the like, is delivered through the catheter to the uterine arteries which quickly become occluded.

The uterus has a dual (or redundant) blood supply, the primary blood supply being from the bilateral uterine arteries, and the secondary blood supply from the bilateral ovarian arteries. Consequently, when both uterine arteries are occluded, i.e. bilateral vessel occlusion, the uterus and the fibroids contained within the uterus are both deprived of their blood supply. However, as demonstrated by Ravina et al., the ischemic effects on the fibroid is greater than the effect on the uterus. In most instances, the fibroid withers and ceases to cause clinical symptoms.

However, many physicians do not possess the training or equipment necessary to perform catheter-based uterine artery embolization under radiologic direction. Accordingly, there are substantially fewer uterine artery embolizations performed, worldwide, each year than hysterectomies for symptomatic uterine fibroids.

Recently, fibroid treatment procedures have been described wherein the uterine arteries are temporarily occluded by an intravaginal device which is non-invasively pressed against the patient's vaginal fornix and clamped or otherwise pressed against tissue bundle with the patient's uterine artery being within the bundle. Pressure on the tissue occludes the underlying uterine artery. While these procedures have shown much promise, in many situations the devices described to date do not always allow for accurate placement of the clamping surfaces.

What is needed, therefore, are devices and methods to detect blood vessels and blood flow in blood vessels, and devices and methods to occlude blood flow in blood vessels such as the uterine arteries that can be used by physicians with limited training and equipment.

SUMMARY OF THE INVENTION

The invention is directed to a relatively non-invasive uterine artery occlusion device and system and the procedure for using the device and system for occluding a female patient's uterine artery. The instruments and their use may be utilized in the treatment of uterine fibroids, dysfunctional uterine bleeding, post partum hemorrhage and other uterine disorders by reducing or terminating blood flow through a patient's uterine artery.

A device embodying features of the invention includes an intrauterine clamp which has a pressure applying or clamping member configured to apply pressure against the exterior of the patient's uterine cervix or against the patient's vaginal fornix. The intravaginal clamp also has a stabilizing or positioning member which is configured to be inserted into the patient's uterine cervix so as to stabilize at least a portion of the interior of the uterine cervix and facilitate the more effective application of pressure by the pressure applying member to the exterior of the cervix or the vaginal fornix to ensure effective occlusion of the patient's uterine artery. The uterine artery occlusion is temporary, and may be partial or complete. The distal end of the clamping member is at or distal to the distal end of the stabilizing member. Preferably, the distal end of the clamping member is about 0.1 to about 1 inch distal to the distal end of the stabilizing member.

One method of occluding a blood vessel comprises clamping the blood vessel effective to compress it so that blood flow through the vessel is reduced, or is abolished. Such clamping of a blood vessel may be direct or may be indirect. Preferably, clamping of a blood vessel effective to compress it is accomplished by applying a non-invasive blood vessel occlusion device to tissue near to a blood vessel (e.g., onto tissue surrounding the vessel). A blood vessel occlusion device may also be applied directly onto a blood vessel effective to compress the blood vessel.

In one embodiment of the invention, a non-invasive blood vessel occluding device (such as a clamp with a sensor) may be applied to a portion of a vaginal wall to detect and/or locate, and to occlude the uterine arteries. A vaginal clamp embodying features of the invention may used to sense the location of a uterine artery adjacent a vaginal wall, and may be used to compress and occlude a uterine artery adjacent a vaginal wall. The vaginal wall may be distended by an occlusion device so as to more closely approach a uterine artery; such an approach may aided by applying pressure or force to the uterus (e.g., by pulling on the uterine cervix). A uterine cervix may be grasped or pulled by any suitable device or implement, including forceps, suction devices, and other instruments, such as a tenaculum.

A non-invasive blood vessel occluding device embodying features of the invention may be a non-invasive intravaginal uterine artery occlusion device, comprising a pair of pressure-applying members having opposed tissue-contacting surfaces on distal portions thereof; at least one supporting shaft extending from a proximal extremity of at least one of the pressure-applying members which is configured to adjust the distance between the opposed tissue-contacting surfaces of the pressure-applying members; and at least one blood flow sensing sensor on one of the opposed tissue-contacting surfaces. An embodiment of a non-invasive blood vessel occlusion device embodying features of the invention may have, for example, a handle, a clamping member configured to apply pressure or force to body tissue, and a sensor for locating a blood vessel.

A pressure-applying member, such as a clamping member, may be, e.g., a jaw or jaws configured to engage a blood vessel or to engage tissue adjacent a blood vessel. A supporting shaft, such as a handle, is preferably configured for manipulating the jaw or jaws. In some embodiments of devices having features of the invention, a pressure-applying member may be attached to a connecting portion that is configured so that a jaw may be placed within a vagina while a handle remains outside a patient's body and available for use by an operator.

The clamping member is preferably provided with a blood flow sensor for locating the blood vessel to be occluded. The sensor may sense sound, pressure, strain, stress, chemical entity, electromagnetic radiation and the like, and may be a combination of such sensors. A sensor is preferably a Doppler ultrasound sensor. The sensor is mounted to the face of a tissue-contacting surface of the clamping member, such as the face of a jaw of a clamp, and is preferably oriented perpendicularly to the clamp face, although other orientations may be employed. Ultrasound energy useful for sensing a location of a blood vessel or of blood flow in a blood vessel has a frequency of less than about 20 MegaHertz (MHz), such as between about 5 MHz and about 19 MHz, and preferably between about 6 MHz and about 10 MHz. In commercially available Doppler sensors the frequency is typically about 8 MHz. For sensors based on electromagnetic energy useful for sensing a location of a blood vessel or of blood flow in a blood vessel, the EM energy should have a wavelength of about 500 nanometers (nm) to about 2000 nm, preferably about 700 nm to about 1000 nm.

A system embodying features of the invention includes an blood vessel occluding device as described above with a blood flow sensor on the clamping member for locating the target blood vessel, and a sensor controller which may include an energy source for the sensor. The sensor controller may be configured to aid in detecting a location of a blood vessel, by, e.g., providing a signal related to the output of a sensor that may be readily used by an operator. A sensor controller may include an energy source configured to provide energy for operating a blood flow sensor.

A method for occluding a uterine artery which embodies features of the invention include advancing the clamping device through the patient's vaginal canal, guiding the stabilizing member of the clamping device through the cervical os, into the cervical canal with the clamping member spaced from the stabilizing member so that the pressure applying surfaces of the clamping member is pressed into the patient's vaginal fornix. Adjustment of the clamping member allows the sensor on the distal end thereof to locate the uterine artery a short distance from the surface of the vaginal fornix. With the clamping member adjacent to the target blood vessel, the clamping device can be closed to compress underlying tissue and thereby occlude the uterine artery. The uterine artery is located with the blood flow sensor on the distal end of the clamping member. Tension may be applied to the uterine cervix with a grasping implement (e.g., by pulling on the uterine cervix) while applying force or pressure to a vaginal wall to occlude a uterine artery.

The invention allows for the non-surgical location and occlusion of blood vessels such as the uterine artery, providing effective therapeutic treatment. Importantly, the present invention allows for the occlusion of a female patient's uterine artery without the need for radiographic equipment or for extensive training in the use of radiographic techniques. The devices and methods are simple and readily used for treating uterine fibroids, dysfunctional uterine bleeding (DUB), adenomyosis, post-partum hemorrhage, and other uterine disorders. The devices, systems and methods embodying features of the invention allow for the separate occlusion of individual uterine arteries which provides effective therapy in those situations in which the uterine anatomy will not allow for the use of a single bilateral artery occlusion device.

These and other advantages will become more apparent from the following detailed description when taken in conjunction with the accompanying exemlary drawings.

DETAILED DESCRIPTION OF THE INVENTION

Figures 1, 2:
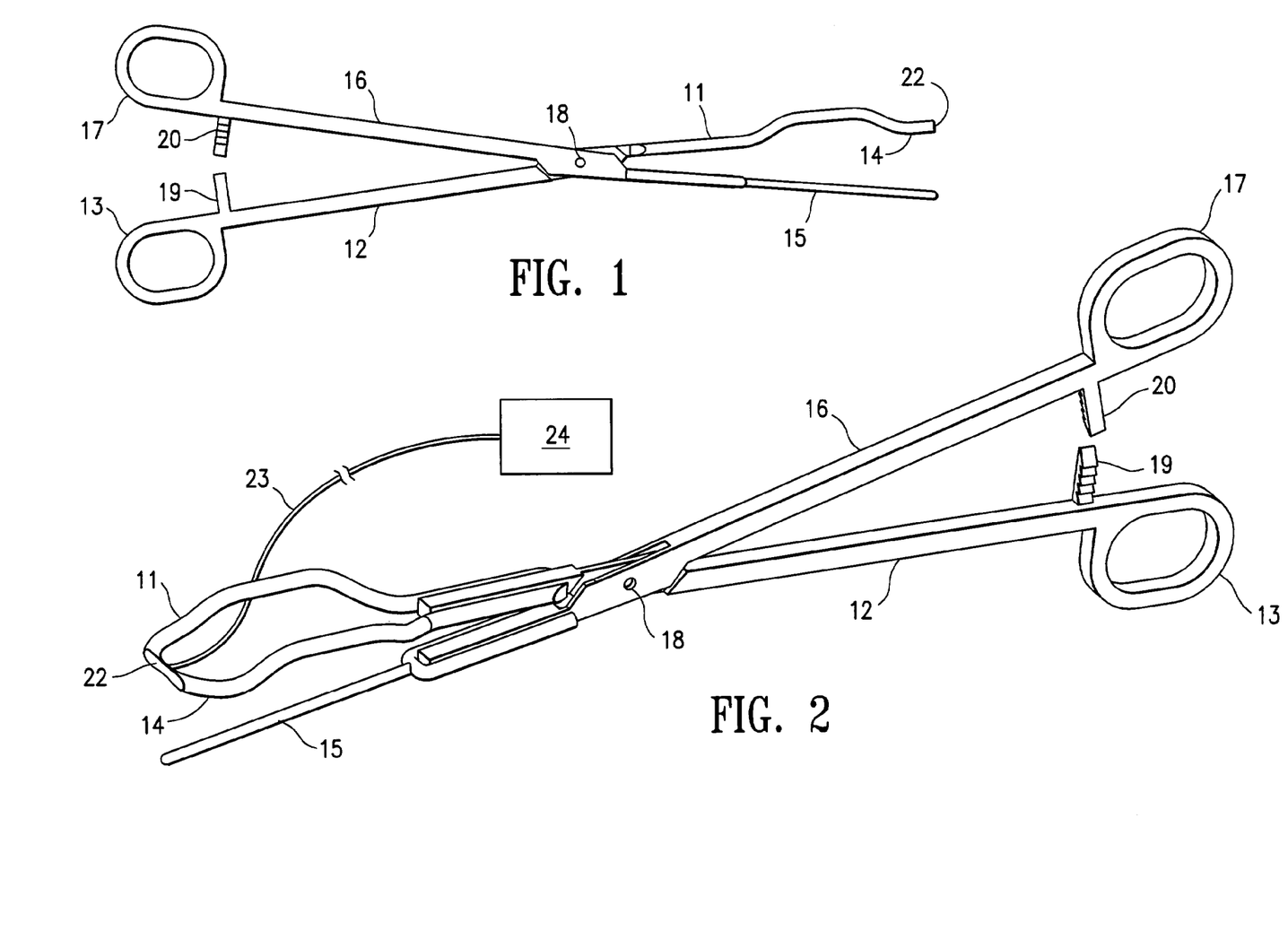
FIG. 1 is an elevational view of a uterine artery clamping device embodying features of the invention in an open configuration.
FIG. 2 is a perspective view of the clamping device shown in FIG. 1.

FIGS. 1 and 2 show a relatively non-invasive intra-uterine occluding clamp 10 embodying features of the invention. The clamp 10 includes a clamping member 11 having an elongated handle 12 with a finger grip 13, and pressure-applying clamping element or jaw 14 on the distal end of the clamping element. The intra-uterine clamp also includes stabilizing member 15 which is configured to readily follow or track the patient's cervical os and cervical canal. The stabilizing member 15 has an elongated handle 16 with a finger grip 17. The clamping member 11 and stabilizing member 15 are pivotally connected to each other at pivot point 18 and rotation of handles 12 and 16, preferably by fingers of an operator's hand engaged through grips 13 and 17 respectively, adjust the spacing between the jaw 14 and the distal portion of stabilizing member 15. Each of the handles 12 and 16 are provided with a ratchet member 19 and 20 respectively which interact to lock the relative positions of the clamping member 11 and the stabilizing member 15.

A uterine artery clamp embodying features of the invention is preferably provided with a blood flow sensor 22, preferably a Doppler ultrasonic sensing system, on the leading surface of the jaw 14. This sensor location allows the operator to more easily guide the jaw 14 to the location of the patient's target uterine artery. Sensor 22 is provided with a signal transmission cable 23 which is operatively connected to sensor control device 24. Cable 23 may be an insulated wire, plurality of wires, optical fiber, waveguide, or other connection effective to carry signals and/or energy or power between a sensor 22 and sensor controller 24.

Sensor 22 may be a blood flow sensor for locating a blood vessel, and may be a passive sensor, configured to detect intrinsic signals indicating the presence of a blood vessel (i.e., a sound sensor, a motion sensor, a pH sensor, or other sensor configured to detect a physical, chemical, electrical, or physiological indication of the location of a blood vessel). In other embodiments, a blood flow sensor for locating a blood vessel may be an active sensor, configured to emit energy or a signal, and configured to detect signals in response to, or derived from, the emitted energy or signal indicating the presence of a blood vessel (i.e., a source of ultrasound having an ultrasound sensor configured to detect ultrasound reflections from a blood vessel, a source of infrared radiation configured to detect reflections from a blood vessel, or other source of energy and a sensor configured to detect a response indicating the location of a blood vessel). The operation of a sensor may be aided by an energy source such as the sensor controller 24. For example, an energy source may provide electrical energy which aids an ultrasound sensor to produce and to detect ultrasound energy (as, e.g., in the MedaSonics® CardioBeat® Blood Flow Doppler with Integrated Speaker (Cooper Surgical, Inc., Trumbull Conn. 06611)). Other commercially available Doppler ultrasound sensors suitable for use in the present invention include the Koven model ES 100X MiniDop VRP-8 probe (St. Louis, Mo.) and the DWL/Neuro Scan Medical Systems' Multi-Dop B+ system (Sterling, Va.).

Figure 3:
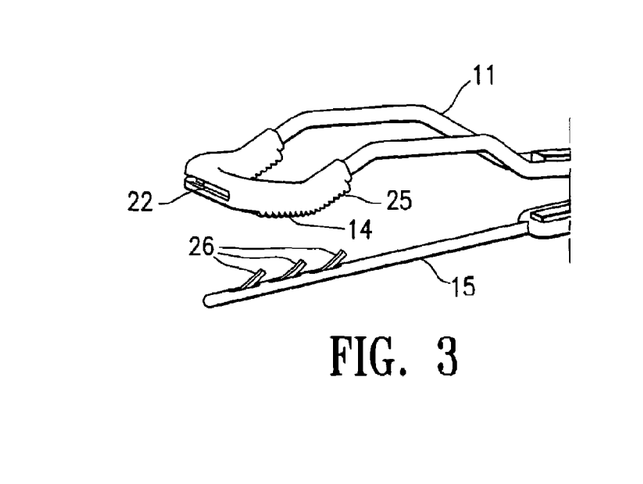
FIG. 3 is an enlarged perspective view of the distal portion of an alternative clamping device having a serrated surface and a plurality of teeth to grasp tissue.
Figure 4:
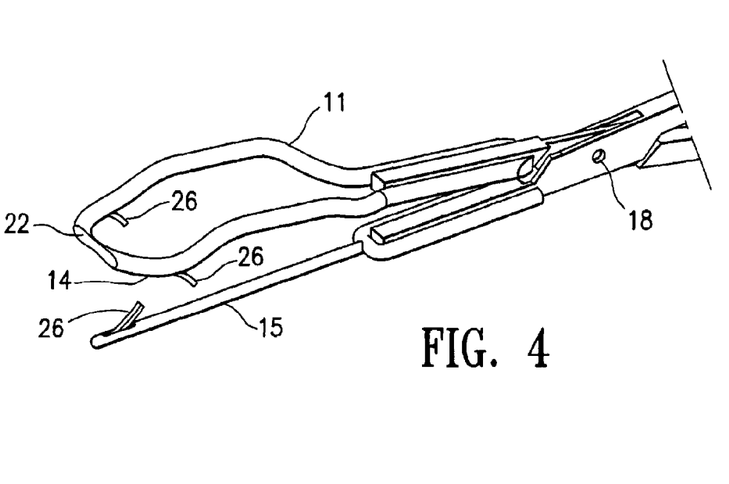
FIG. 4 is an enlarged perspective view of an alternative clamping device in which the clamping element and the stabilizer element are provided with teeth to grasp tissue.

As shown in FIG. 3 jaw 14 may be provided with a serrated, tissue-grasping surface 25 configured to engage and hold onto tissue when jaw 14 is pressed into tissue of the patient's vaginal fornix. As shown in FIG. 4, one or both of the jaw 14 and/or stabilizer 15 may have retractable fingers or teeth 26 to better secure the contacting members to the target tissue.

Figure 5:
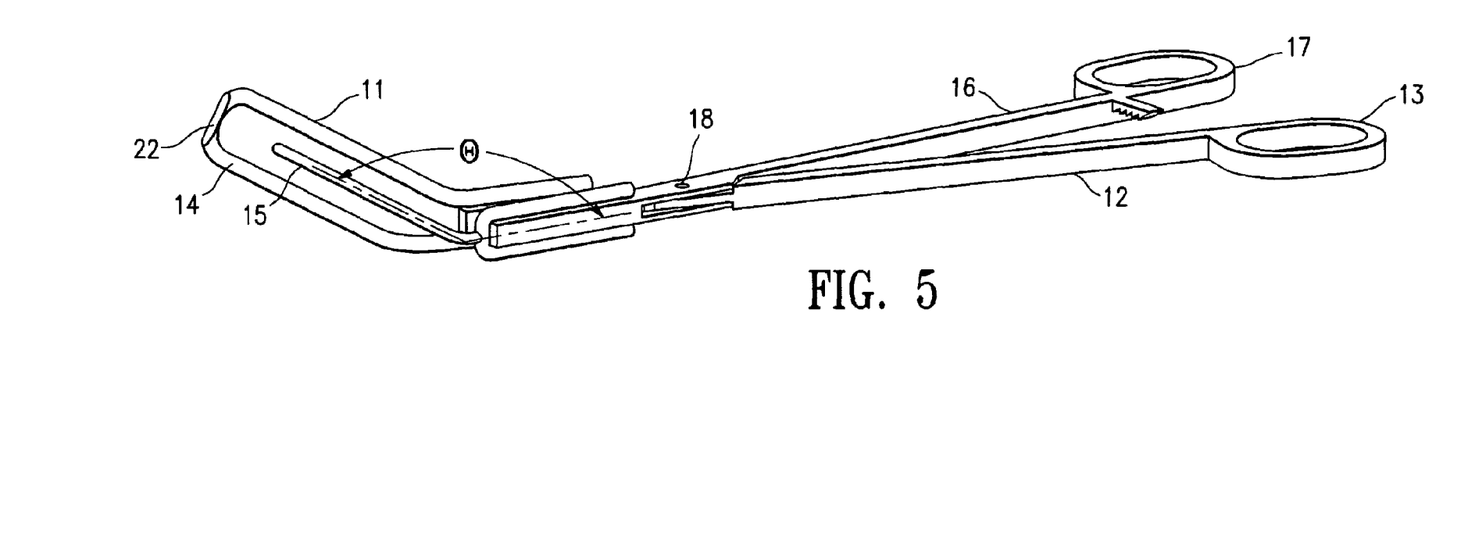
FIG. 5 is a schematic illustration of the intrauterine clamp in position to occlude a female patient's uterine artery.

FIG. 5 illustrates an alternative embodiment wherein the clamping member 11 and the stabilizing member 15 are oriented at an angle θ with respect to the handles 12 and 16. The angulation provides a more direct attack angle to facilitate insertion of the stabilizing member 15 into the patient's cervix and direction of the jaw 14 toward a desired location at the patient's vaginal fornix to facilitate location and occlusion of the patient's uterine artery. Suitable angulation θ of the jaw 14 and stabilizer 15 is about 100° to about 175°, preferably about 130° to about 160°.

Closure of a blood vessel, which may be partial or total, is effected by pressure applied through the wall of the patient's vaginal fornix. Sufficient pressure or force applied to the tissue of the vaginal wall to compress and to at least partially occlude the underlying uterine artery. The blood flow sensor for detecting or locating the uterine artery should be disposed on the leading face off the clamping element and generally perpendicular to the tissue-contacting surface of a jaw 14 to be effective.

A non-invasive blood vessel occluding device embodying features of the invention may be configured to lock into a clamping position. Such a locked configuration may be temporary and releasable, or may be permanent. Non-invasive blood vessel occluding devices embodying features of the invention may have a locking mechanism, such as a ratchet, configured to hold at least one pressure-applying member in a pressure-applying position. Such locking mechanisms may include a release mechanism effective to allow the cessation of pressure or force application when desired. Thus, a non-invasive blood vessel occlusion device embodying features of the invention may be configured to release a locking mechanism effective to relieve the occlusion of a blood vessel by ending the application of pressure or force that had been previously applied to occlude a blood vessel.

The uterine arteries in human females are located adjacent the vaginal mucosa at a location within a few centimeters (cm) of the vaginal fornix. As a result, for accessing and occluding a uterine artery from within the patient's vaginal canala, the dimensions of a vagina determine what size clamping device is suitable, taking into consideration that the clamping device should readily reach the vaginal fornix and be operated from outside of a patient's body. For example, a clamping device may be between about 5 to about 16 inches in length, preferably between about 6 inch to about 12 inches in length for most applications.

Figure 6:
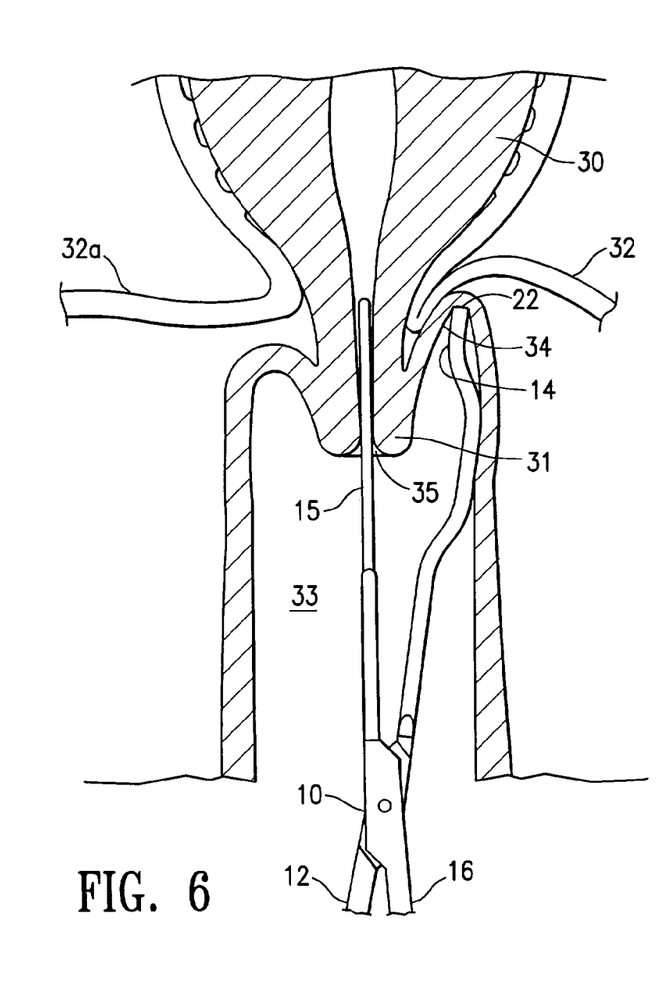
FIG. 6 is a perspective view of an alternative embodiment in which the clamping element and the stabilizing element are angled with respect to the handles of the clamp.

FIG. 6 schematically illustrates in part a human female reproductive system, including a uterus 30, uterine cervix 31, uterine artery 32, vaginal canal 33 and vaginal fornix 34. A method of using the uterine artery clamp embodying features of the invention includes introducing the clamp 10 into the patient's vaginal canal 33 and advancing the clamp therein until the distal portions of the clamp are adjacent to the patient's uterine cervix 31. The position of the handles 12 and 16 are adjusted to increase the spacing between the jaw 14 and the distal portion of the stabilizer 16. The distal end of the stabilizer is guided through the cervical os 35 into the uterine cervix. The distal end of jaw 14 is urged against the vaginal fornix 34 and 14. With the guidance of the Doppler sensor 22, the pressure applying surface of the jaw is positioned as close as possible to the patient's uterine artery 32. Sufficient pressure is applied to the uterine artery 32 or the tissue surrounding the uterine artery by jaw 14 to facilitate occlusion of the uterine artery. The handles 12 and 16 are locked by ratchet members 19 and 20 to press the jaw 14 against the tissue between the jaw 14 and the stabilizer 15. The clamped position is maintained for about 0.5 to about 48 hours, preferably about 1 to about 24 hours for effective therapeutic treatment of a uterine disorder, e.g. for fibroids, PPH, DUB and the like. Blood flow sensor 22 is effective to locate uterine artery 32 by detecting blood flow and monitoring the treatment by detecting the lack of blood flow in the artery. Blood flow in the left uterine artery 32 may be similarly occluded, by a separate uterine artery clamp of the same design or the same clamp can be used on the other side after release of the occlusion of the right uterine artery 32a.

The ratchet members 19 and 20 are preferably releasable so that clamping member 11 of clamping device 10 can be released after the limited treatment time to re-establish blood flow to the uterine tissue.

Figure 7:
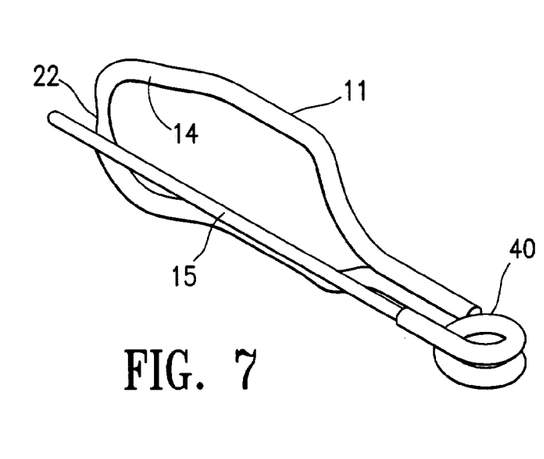
FIG. 7 is a perspective view of an alternative embodiment in which the spacing between the stabilizing member and the clamping member is adjusted by a spring coil.
Figure 8:
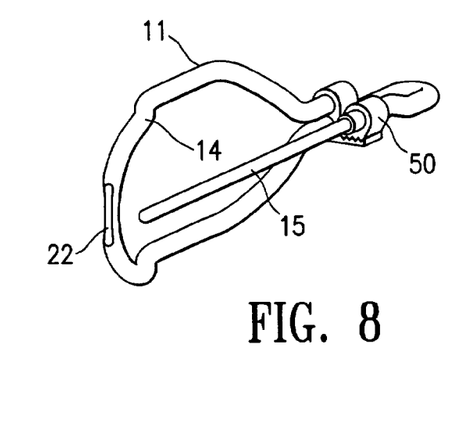
FIG. 8 is perspective view of an alternative embodiment in which the spacing between the stabilizing member and the clamping member is adjusted by a rack and pinion arrangement.

FIGS. 7 and 8 illustrate alternate clamp design wherein the spacing between the jaw 14 and stabilizer 15 is controlled by a spring 40 as shown in FIG. 7 and a rack and pinion mechanism 50 as shown in FIG. 8. A variety of other means may be employed to open and close the jaw 14 and stabilizer 15.

Uterine artery clamp 10 embodying features of the invention may be made from any suitable material or combination of materials, including metals such as stainless steel and superelastic shape memory alloys such as nickel titanium alloys having a stable austenite phase at body temperature, high strength plastics, ceramics, and other materials known in the art. Biocompatible polymers such as polycarbonate, polysulfone, polyester, polyacetal and a variety of fluoropolymers can be suitable for a variety of embodiments of the invention. The device or system may be designed for single use (disposable) or may be sterilizable and capable of multiple use.

While particular forms of the invention have been illustrated and described, it will be apparent that various modifications can be made to the invention and that individual features shown in one embodiment can be combined with any or all the features of another embodiment described herein. Accordingly, it is not intended that the invention be limited to the specific embodiments illustrated. It is therefore intended that this invention be defined by the scope of the appended claims as broadly as the prior art will permit. Terms such as "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action.

What is claimed is:

1. An intravaginal clamping device for occluding a portion of a female patient's uterine artery adjacent to a region of the patient's vaginal fornix, comprising:
   a. a stabilizing member which has a cylindrical distal end configured to extend into the patient's uterine cervix;
   b. a clamping member with a clamping element at the distal portion thereof which is configured to fit about an exterior side portion of the patient's uterine cervix and which has a leading, pressure applying surface on the distal end that is at or extends beyond the distal end of the stabilizing member and which has a width is sufficient to be pressed against the region of the patient's vaginal fornix adjacent to the exterior side portion of the patient's uterine cervix to occlude the portion of the patient's uterine artery adjacent to the region of the patient's vaginal fornix; and
   c. a blood flow sensor on the leading pressure applying surface of the distal end of the clamping member to detect the location of the uterine artery to monitor the blood flow therethrough.

2. The intravaginal clamping device of claim 1 wherein a connector is provided between the clamping member and the stabilizing member to adjust spacing between the clamping member and the stabilizing member.

3. The intravaginal clamping device of claim 2 wherein the connector is a pivotal connection between the clamping member and the stabilizing member.

4. The intravaginal clamping device of claim 1 wherein both the clamping member and the stabilizing member have elongated handles.

5. The intravaginal clamping device of claim 4, wherein the handles have an interconnecting locking mechanism which provide a locked configuration effective to retain the clamping member in a pressure-applying configuration.

6. The intravaginal clamping device of claim 1 wherein the clamping member has a pressure applying surface which generally lies in a plane perpendicular to a plane in which the handles rotate.

7. The intravaginal clamping device of claim 1 wherein the stabilizing member is longer than the clamping member.

8. The intravaginal clamping device of claim 1 wherein the clamping element is paddle-shaped.

9. The intravaginal clamping device of claim 8 wherein the paddle-shaped clamping element is at least in part formed of a wire frame.

10. The intravaginal clamping device of claim 1 wherein the clamping member and the stabilizing member are curved.

11. The intravaginal clamping device of claim 1, wherein the clamping element is releasably secured to a handle.

12. The intravaginal clamping device of claim 1, wherein the blood flow sensor is a Doppler ultrasound sensor.

13. The intravaginal clamping device of claim 12, wherein the Doppler ultrasound sensor is configured to sense ultrasound energy having a frequency of between about 5 MHz and about 20 MHz.

14. The intravaginal clamping device of claim 12, wherein the Doppler ultrasound sensor is configured to sense ultrasound energy having a frequency of between about 6 MHz and about 10 MHz.

15. The intravaginal clamping device of claim 1, wherein the clamping element has a length between about 1 and about 6 inches.

16. The intravaginal clamping device of claim 1, wherein the clamping member has a length between about 2.5 inches and about 4.5 inches.

17. The intravaginal clamping device of claim 1, wherein the distal end of the clamping element is disposed distal to the distal end of the stabilizing member by a distance of about 0.1 inch to about 1 inch.

18. The intravaginal clamping device of claim 1, wherein the pressure apply surface on the distal end of the clamping element has a width of about 0.5 inch to about 3 inches.

19. The intravaginal clamping device of claim 1, wherein the clamping element is formed at least in part of a loop-shaped wire frame.

20. A system for occluding a female patient's uterine artery, comprising:
   a. a uterine artery clamping device which has
      i. a clamping member which has an elongated handle and a clamping element with a distal end and a pressure applying surface on the distal end configured to occlude a uterine artery when the pressure applying surface is pressed against the patient's vaginal fornix,
      ii. a stabilizing member which has an elongated handle at an obtuse angle with respect to the elongated handle of the clamping member and which has a cylindrical distal end that is configured to enter the patient's uterine cervix and that is at or proximal to the distal end of the clamping element; and
   b. an artery location sensor secured to the pressure applying surface on the distal portion of a clamping element to ensure that pressing the pressure applying surface of the clamping element against the patient's vaginal fornix occludes the patient's uterine artery.

21. The system of claim 20 wherein the clamping device has a pivotal connection between the clamping member and the stabilizing member so that rotation of the handles about the pivotal connection adjusts spacing between the clamping member and the stabilizing member.

22. The system of claim 21 including an elongated signal transmitting member having a proximal end and a distal end and being secured at its distal end to the artery locating sensor and having a connector on its proximal end configured to be connected to a sensor controller.

23. The system of claim 20, wherein the artery location sensor is a Doppler ultrasound sensor.

24. The system of claim 21 wherein the handles have a locking mechanism to provide a locked configuration effective to retain the clamping member and the stabilizing member in a pressure-applying configuration.

25. The intravaginal clamp of claim 22 wherein the connector is a spring.

26. The intravaginal clamp of claim 22 wherein the connector is a rack and pinion mechanism.

* * * * *